United States Patent [19]
Carter et al.

[11] Patent Number: 5,958,886
[45] Date of Patent: Sep. 28, 1999

[54] CARNITINE-CONTAINING PEPTIDES AND A METHOD FOR USING THE SAME

[75] Inventors: A. Lee Carter; Frederick H. Leibach; David F. Lapp, all of Augusta; Vadivel Ganapathy, Martinez, all of Ga.; Gianfranco Fornasini, Gaithersburg, Md.

[73] Assignee: Sigma-Tau Pharmaceuticals, Inc., Gaithersburg, Md.

[21] Appl. No.: 09/006,194

[22] Filed: Jan. 13, 1998

[51] Int. Cl.⁶ .................................................... A61K 38/05
[52] U.S. Cl. ................................ 514/19; 514/18; 530/331
[58] Field of Search .................................. 514/2, 17–19; 530/331

[56] References Cited

U.S. PATENT DOCUMENTS

| | | | |
|---|---|---|---|
| 4,537,772 | 8/1985 | Alexander | 514/9 |
| 5,512,671 | 4/1996 | Piantadosi | 536/26.1 |
| 5,607,691 | 3/1997 | Hale | 424/449 |

FOREIGN PATENT DOCUMENTS

| | | |
|---|---|---|
| 0514359 | 11/1992 | European Pat. Off. . |
| 2474489 | 7/1981 | France . |

OTHER PUBLICATIONS

Tewari, J. Neurosci Res 40, 371, 1995.

*Primary Examiner*—Cecilia J. Tsang
*Assistant Examiner*—David Lukton
*Attorney, Agent, or Firm*—Oblon, Spivak, McClelland, Maier & Neustadt, P.C.

[57] ABSTRACT

A carnitine-containing peptide sequence, which is a substrate for a mammalian peptide transport system, which contains at least one carnitine residue with at least one amino acid residue bonded thereto via an amide or ester linkage.

7 Claims, No Drawings

CARNITINE-CONTAINING PEPTIDES AND A METHOD FOR USING THE SAME

BACKGROUND OF THE INVENTION

1. Field of the Invention

The present invention relates to carnitine-containing peptides which are capable of delivering exogenous carnitine across cell membranes and intestinal mucosae to provide carnitine to a mammal.

2. Description of the Background

Carnitine is a naturally occurring amino acid required for mitochondrial oxidation of long-chain fatty acids. It is a betaine derivative found in skeletal muscle and liver, and acts as a carrier of fatty acids across the mitochondrial membrane into the mitochondrial matrix, where the fatty acids combine with coenzyme A (CoA) to form acyl CoA. Carnitine has the formula:

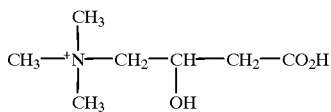

Juvenile humans possess a carnitine transport system in the intestine, however, it appears that this active transport system becomes less active in adulthood, resulting in low carrier-mediated absorption of carnitine. Passive diffusion is the dominant method of crossing the intestinal barrier for carnitine, but is not efficient because carnitine compounds are quite polar. Consequently, adult humans are largely unable to assimilate large amounts of carnitine. Carnitine deficiency is associated with a number of disorders, one of which is a slowly progressive proximal polymyopathy with lipid storage in muscle fibers. Unfortunately, without the carnitine transport system, adult humans are unable to assimilate exogenous carnitine across cell membranes and intestinal mucosae to remedy the deficiency.

Thus, a need exists for a means by which carnitine may be effectively transported across cell membranes and intestinal mucosae in mammals, particularly in humans.

SUMMARY OF THE INVENTION

Accordingly, it is an object of this invention to provide a means for transporting exogenous carnitine across cell membranes and intestinal mucosae in mammals.

It is also a specific object of the present invention to provide a peptide sequence containing carnitine, which is capable of being transported across cell membranes and intestinal mucosae in mammals by endogenous peptide transport systems.

It is a further object of their invention to enhance the bio-availability of L-carnitines to mammals.

These objects and others are provided by a peptide sequence containing carnitine, which is transportable on a peptide carrier to deliver carnitine to a mammal in need thereof.

The term carnitine is used herein to represent not only carnitine, per se, particularly L-carnitine, but acyl carnitines as well. This includes $C_{2-18}$ substituted carnitines, including acetyl, propionyl, butyryl, valeryl, palmitoyl and related carnitines, particularly acyl-L-carnitines.

DETAILED DESCRIPTION OF THE PREFERRED EMBODIMENTS

The present invention is predicated, in part, upon the discovery that certain peptide sequences containing carnitine developed by the inventors can be actively or positively transported across cell membranes and intestinal mucosae in mammals by endogenous peptide transport systems. Generally, the present invention provides peptide sequences containing carnitine having an overall length of from 1 to about 20 amino acid residues. More preferably, the carnitine transport system of the present invention is used to deliver carnitine-containing peptides containing from about 1 to 10 amino acid residues.

In accordance with the present invention, one or more carnitine residues may be incorporated into or at the amino end of a peptide sequence.

Thus, the present invention provides a carnitine-containing peptide sequence having at least one carnitine residue and at least one amino acid residue bonded thereto via either an amide or ester linkage.

More specifically, the present invention provides carnitine-containing peptide sequences having either single or multiple, such as two, three, four or five, for example, carnitine residues either at the terminal end of or incorporated into a peptide sequence of from 1 to up to about 20 amino acid residues.

Thus, for example a single carnitine-containing peptide of the present invention may have the formula:

where C is a carnityl residue which may be bonded to $A_1$ which is an amino acid and/or $A_2$ which is an amino acid both bonded by an amide or ester linkage, noting that, due to structural considerations, when C is incorporated into a peptide sequence, both amide and ester linkages are required.

As noted above, the present peptides may also contain multiple carnitine residues and have the formula:

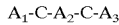

or

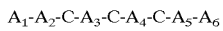

for example, where $A_1$–$A_6$ are the same or different amino acids and C is a carnitine residue.

For example, in accordance with the present invention, peptides having carnitine at the amino terminal position are provided of the formula (I):

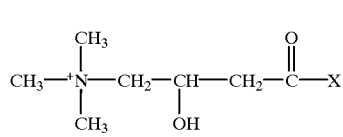

(I)

wherein X is an amino acid sequence of from 1 to about 20 amino acid residues and R is H or any acyl linear carbon moiety of 2–18 carbon atoms. For this type of peptide sequence, peptide bonds are formed through the carboxy terminus of carnitine.

However, in accordance with the present invention, peptide sequences are also provided wherein carnitine is incorporated into the peptide sequence via amide linkage at the carboxy terminus of carnitine and ester linkage at the hydroxy group of carnitine. Such peptide sequences have the formula:

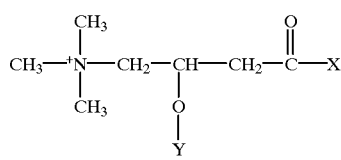

(II)

wherein X is an amino acid sequence of from 1 to about 20 amino acid residues, and Y is an amino acid sequence of from about 1 to about 20 amino acid residues or an acyl linear group of 2–18 carbon atoms, wherein the total of (X+Y) is from 2 to about 20 amino acids. In formula (II) above, where Y is an amino acid sequence the first amino acid residue of Y is joined to the hydroxyl oxygen at the carboxy terminus thereof.

Additionally, the present invention also provides peptides sequences of the formula:

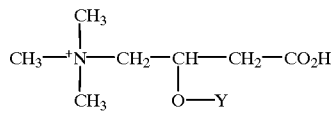

(III)

where Y is an amino acid sequence as defined above for formula (II).

Generally, in any of formula (I), (II) or (III), the following amino acids of the L-configuration may be used: glycine, alanine, valine, leucine, isoleucine, serine, threonine, cysteine, cystine, methionine, aspartic acid, glutamic acid, asparagine, glutamine, lysine, hydroxy-lysine, histidine, arginine, phenylalanine, tyrosine and tryptophan. Additionally, in accordance with the present invention, proline and/or hydroxy proline may also be used.

Generally, the peptide sequences of the present invention may be prepared using well known reactions, such as the solid-phase synthesis scheme of Merrifield using the $N^\alpha$-tert-butyloxycarbonyl (Boc) protecting group using graduated acidolyis or the solid-phase synthesis scheme using the base-labile $N^\alpha$-tert-fluorenylmethyloxycarbonyl (Fmoc) group of Carpino. See *Synthetic Peptides*, chp. 3 "Principles and Practice of Solid-Phase Peptide Synthesis, edited by G. A. Grant (Freeman 1992).

In preparing the present peptide sequences, the hydroxyl group of carnitine may be protected, when desired, by standard hydroxyl-protecting groups, such as tert-butyldimethyl silyl chloride for Fmoc synthesis, and Bzl for Boc synthesis. See Becker et al, *Eur. J. Biochem*, 185:79–84 (1989) and Penke et al, Eleventh American Peptide Symposium Abstracts, pp P-335 (1989). Such syntheses are well known in the art.

The carnitine-containing peptides of the present invention are delivered across cell membranes and intestinal mucosae by endogenous peptide transport systems, thereby providing an exogenous source of carnitine for a mammal. Thus, the present peptides provide an exogenous source of carnitine to adult humans as these peptides are readily assimilated by the human peptide transport system enhancing carnitine bioavailability.

The following non-limiting examples of carnitine-containing peptides which may be used in accordance with the present invention are noted. The standard three-letter abbreviations for amino acids are used therefore:

| | | |
|---|---|---|
| Glycine: Gly | Methionine: Met | Phenylalanine: Phe |
| Alanine: Ala | Aspartic Acid: Asp | Tyrosine: Tyr |
| Valine: Val | Glutamic Acid: Glu | Tryptophan: Trp |
| Leucine: Leu | Asparagine: Asn | Proline: Pro |
| Isoleucine: Ile | Glutamine: Gln | Hydroxyproline: Hyp |
| Serine: Ser | Lysine: Lys | |
| Threonine: Thr | Hydroxylysine: Hyl | Cystine: Cys-Cys |
| Cysteine: Cys | Histidine: His | Arginine: Arg |

Carnitine is abbreviated as C irrespectively upon whether the bond with the adjacent amino acid is via the carboxy or hydroxy group. Representative sequences of the type where C is bonded through the carboxy group are:

C-Gly
C-Gly-Ala
C-Ala-Ala
C-Ala-Val-Leu
C-Gly-Val-Ala-Leu
C-Gly-Ala-Leu, Val-Ala
C-Ala-Leu-Ser-Thr-Val-Cys
C-Thr-Leu-Val-Ile-Cys-Asn-Phe or
C-Thr-Val-Ile-Arg-His-Phe-Trp-Glu

Representative sequences of the type where C is bonded through the hydroxy group are:

C-Gly
C-Ala-Gly
C-Ala-Ala
C-Ala-Val-Leu
C-Gly-Leu-Val-Ala
C-Thr-Leu-Ile-Gly-Ala
C-Thr-Val-Leu-Trp-Glu-Arg
C-Arg-Val-Glu-Asp-Met-Arg-Trp
C-Phe-Met-Val-Leu-Ile-Glu-Arg-Ser.

Representative sequences of the type where C is incorporated in a peptide sequence using both carboxy and hydroxy linkages are:

Gly-C-Ala-Ala-C-Leu

Ala-Gly-C-Leu-Val-C-Glu-C

Ala-Gly-Leu-C-Val-C-Leu-C-Glu-Asp or

Ala-Gly-Leu-Val-Asp-Met-C-Arg-C-Glu

As noted above these sequences may contain, in general, up to about five carnitine residues with from 1 to up to about 20 amino acids with the proviso that there be at least about one amino acid residue use per carnitine residue.

The carnitine-containing peptides of the present invention may be orally administered as peptides, either dry or in solution, by themselves or used as additives for human and veterinary foods. They may also be administered topically or by injection. Alternative routes of administration include inhaled aerosol and rectal suppositories.

Generally, the carnitine comprising peptides of the present invention are minimum as the amount of carnitine derivatized administered in the range of about 100 μg to about 100 mg/kg body weight measured as the amount of carnitine administered per day as needed for a human and from about 10 μg to about 50 mg per day for mammals of varying size, such as rabbits, cats, dogs, cows, sheep, or horses, for example. Thus, irrespective of whether the present peptides are used as food additives or feed additives, the above ranges will be taken into account as a guide when considering how much peptide is used in the additive. In general, however, either food or feed additives will contain from about 0.01% by weight to about 10% by weight of the food or feed additive.

For example, when used as a food additive, the present peptides may be mixed with salt, pepper, dried herbs and/or spices, such as celery seed, oregano, thyme, dill or rosemary. Any conventional base, now commercially available, may be enriched with the present peptides in order to obtain an enriched food or feed substance.

Having described the present invention, reference will not be made to certain examples which are provided solely for purposes of illustration and which are not intended to be limitative.

EXAMPLE 1

Carnityl-alanyl-alanine (CAA) is a peptide derivative of carnitine. In this experiment, the ability of CAA to compete with glycyl-sarcosine for transport via the peptide carrier was studied in Caco-2 cells. These cells are a good model system for the human intestine and they express the peptide carrier as does the human intestine. Glycyl-sarcosine is a standard substrate for the peptide carrier. If CAA is taken up by the peptide carrier it is expected to compete with glycyl-sarcosine for transport via the carrier and thus inhibit the transport. The experiments show that CAA inhibited the transport of glycylsarcosine by 35% at 10 mM and by 80% at 20 mM. This indicates that CAA is recognized by the peptide carrier as a substrate. Free carnitine does not inhibit glycyl-sarcosine transport under similar conditions, indicating that free carnitine is not transported via the peptide carrier.

EXAMPLE 2

In this experiment, Xenopus (frog) oocytes which were made to express the peptide carrier from human intestine by injection of its peptide transporter mRNA were used to study the transport of CAA via the carrier. The peptide carrier uses the energy from a proton gradient and peptide transport via the carrier leads to a transfer of positive charge into the oocytes. This charge transfer can be monitored using the electrophysiological approach. If CAA is transported via the peptide carrier, exposure of the oocytes to CAA is expected to result in the transfer of positive charge. These experiments show that exposure of the oocytes to 10 mM CAA induced charge transfer. This charge transfer was qualitatively comparable to the charge transfer found when the oocytes were exposed to 10 mM glycyl-sarcosine.

From the above experiments, it is quite clear that CAA is transported via the intestinal peptide carrier. The affinity is in the millimolar range, which indicates that the peptide carrier-mediated transport of CAA has a high capacity. This characteristic is suitable to increase the intestinal absorption of carnitine as CAA via the peptide carrier.

Having described the above invention, it will now be apparent to one of ordinary skill in the art that many changes and modifications may be made to the above embodiments without departing from the spirit and the scope of the present invention.

What is claimed is:

1. A carnitine-containing peptide, which is a substrate for a mammalian peptide transport system, wherein said peptide has the sequence:

carnitine-alanyl-alanine.

2. A pharmaceutical composition for treating a carnitine-mediated condition in a mammal in need thereof, which comprises:

a) an effective amount of the peptide of claim 1, and b) a pharmaceutically acceptable carrier.

3. A method of treating a carnitine-mediated condition in a mammal in need thereof, which comprises administering to said mammal an effective amount of the peptide of claim 1.

4. The method of claim 3, wherein said mammal is human.

5. A carnitine-enriched food substance, comprising an effective amount of the peptide of claim 1.

6. A carnitine-enriched animal feed substance, comprising an effective amount of the peptide of claim 1.

7. A food or feed additive, which comprises an effective amount of the peptide of claim 1.

* * * * *